United States Patent [19]

Lenox et al.

[11] Patent Number: 4,672,968
[45] Date of Patent: Jun. 16, 1987

[54] HEADWEAR WITH BUILT-IN COOLING MEANS

[76] Inventors: Jerril C. Lenox; Jesse Solis, both of P.O. Box 3156, Riverside, Calif. 92519

[21] Appl. No.: 771,031
[22] Filed: Aug. 30, 1985
[51] Int. Cl.[4] ............................. A42C 5/04; A61F 7/00
[52] U.S. Cl. ..................................... 128/380; 2/171.3; 128/400
[58] Field of Search ................. 128/380, 400; 2/171.3; 62/259.3

[56] References Cited

U.S. PATENT DOCUMENTS

| | | | |
|---|---|---|---|
| 1,739,082 | 12/1929 | Simmons et al. | 98/42.08 |
| 3,302,551 | 2/1967 | van Belle et al. | 98/42.07 |
| 3,629,868 | 12/1971 | Greenlee | 2/171.3 X |
| 3,649,964 | 3/1972 | Schoelz et al. | 2/171.3 X |
| 4,546,496 | 10/1985 | Lewis | 2/171.3 |

Primary Examiner—Anton O. Oechsle
Attorney, Agent, or Firm—John H. Crowe

[57] ABSTRACT

A headpiece with two built-in fan units for cooling the face and back of the neck of a surgeon while he or she is performing surgery. Each of the fan units has a fan blade mounted perpendicularly within a cylindrical housing in close tolerance with the inner wall of the housing and includes an electric motor having a drive shaft to which the fan blade is attached. The motor and fan blade assembly is supported by vanes interconnecting it with the cylindrical housing which extend radially outwardly from the axis of the assembly. The headpiece has a frame that fits a wearer's head like a hat and supports the two fan units, one in front and the other in back of the frame. The frame also supports a power source for the two fan motors and other components of circuitry which permit adjustment of the speed of each motor for optimum cooling effect. The fan units are pivotally mounted and manually adjustable to different angular positions for control of the direction of airflow in front and back of the wearer's head.

9 Claims, 6 Drawing Figures

HEADWEAR WITH BUILT-IN COOLING MEANS

BACKGROUND OF THE INVENTION

This invention relates generally to headwear with self-contained cooling means and more particularly to such headwear in the form of a surgeon's headpiece for use during surgical operations.

A complex surgical operation is a grueling, stress-laden experience for even the most skilled of surgeons. Such operations are normally performed in operating rooms of hospitals under powerful incandescent lights that radiate a great deal of heat which, combined with the stress experienced by surgeons performing operations in which human life often hangs in the balance, cause much discomfort to surgeons performing their work in the glare of the lights. Such a surgeon is dressed in a gown, surgical gloves and a covering and mask for his head that leaves only his eyes and a small part of his face exposed. In performing the intricate steps of a complicated operation, the surgeon generally has his hands occupied to such an extent that a nurse must periodically mop his brow to remove perspiration, particularly after an extended period of time in the operating theater. As he goes through the various steps of a complicated operation, the surgeon often bends his head and exposes a part of the back of his neck to the intense heat of the overhead lights. The longer the operation takes, the more the surgeon suffers from heat exposure and nervous tension. When it is considered that operations often take many hours, sometimes with more that one surgeon at work on a patient, it is not surprising that such a surgeon leaves an operating room at the end of the long ordeal with his gown and other wearing apparel wringing wet. Up to now, no way of providing adequate cooling comfort to surgeons during operating procedures has been made available insofar as we are aware, in spite of the fact that an urgent need for such an expedient has long existed.

The prior art contains disclosures of various types of headwear with built-in cooling means, but none of these disclosures relates to a headpiece for use by an operating surgeon, or anything that would satisfactorily serve that purpose, insofar as we are aware. Typical of prior art references containing such disclosures are the following U.S. Patents to William A. Waters: U.S. Pat. Nos. 3,391,407; 3,543,415; 3,381,198; 4,141,083; and 4,238,857. Each of the first two of these patents discloses a helmet with a battery-operated fan and cooperating temperature control means mounted in its dome, the third and fourth disclose air conditioning units for headwear, comprising electric motors, and fans, removably secured within lightweight housings, and the fifth relates to another self-contained air conditioning unit for headwear with means for blowing warm or cool air onto the wearer. U.S. Pat. No. 3,735,423 to Julius Droz discloses a hat with a hollow chamber in which is mounted a fan, said chamber having a discharge port with vanes to direct the air downward. U.S. Pat. No. 4,101,981 to Boden discloses a hat or cap having a crown with ventilaion openings including a top opening beneath which a baffle is supported. The baffle enables "free flow of air" through the space thereabove within the hat or cap and "blocks direct passage of sunlight into [said] hat or cap through the top opening."

In none of the prior art fans mounted in or on headwear of which we are aware is sufficient air flow achieved to provide any significant cooling effect therefrom. The Waters headwear, for instance, relies, for the most part, upon air conditioning attachments for such cooling effect, not on fans alone. Each of the above-mentioned (prior art) fan arrangements has a fan blade mounted within a relatively large chamber, the chamber typically being provided with grid members or the like at its intake and outlet openings that hinder the free flow of air therethrough. As a consequence, while there is some air circulation around the head of one wearing such headwear, there is not enough circulation to provide any significant degree of comfort to the wearer, especially if he is doing something involving physical effort, such as, for example, mowing a lown, on a warm summer day. Even if the flow of air is not hindered by grid means, or the like, a fan blade turning in a relatively large space cannot create the kind of cooling effect that a more focused or channelized stream of air can achieve. Thus, none of the prior art headgear of which we are aware would be suitable for use by a surgeon operating for several hours under the hot lights of an operating room.

SUMMARY OF THE INVENTION

We have now, by the present invention, provided a headpiece with cooling means particularly suitable for use by a surgeon under operating conditions. In the preferred form of the headpiece, the cooling means serves to create strong air currents on either or both of his face and the back of his neck for many hours in the operating room. The headpiece, again in its preferred form, includes a rigid headband for fitting the headpiece to a surgeon's head over his normal head covering and providing support above his face and the back of his neck for a pair of battery-powered motor and fan assemblies, each including a fan blade mounted within a cylindrical housing open at both ends. The fan blade is positioned perpendicularly to the axis of the housing, and is of a diametric size to turn within the housing in close tolerance with its inner wall surface. One of the housings serves to direct a stream of air toward the face of the surgeon and the other directs such a stream toward the back of his neck. The motor is positioned concentrically within the cylindrical housing and integral vanes or webs, preferably three in number, extend radially outwadly from the motor to interconnection with the housing. This vane arrangement presents minimal obstruction to the flow of air through the housing and resides at the heart of our invention because it, more than any other feature, permits the substantially unobstructed flow of air past the motor to the fan blade, from whence the air is blown away from the housing in the form of a strong current. We tried numerous other ways of mounting the fan motor withing its housing, including the use of mounting means such as disclosed in the prior art, but none resulted in the production of the strong current of air made possible by our motor and fan combination with its radial vanes supporting a fan blade within a closely confining cylindrical housing.

DESCRIPTION OF PREFERRED EMBODIMENTS

Figure 1:
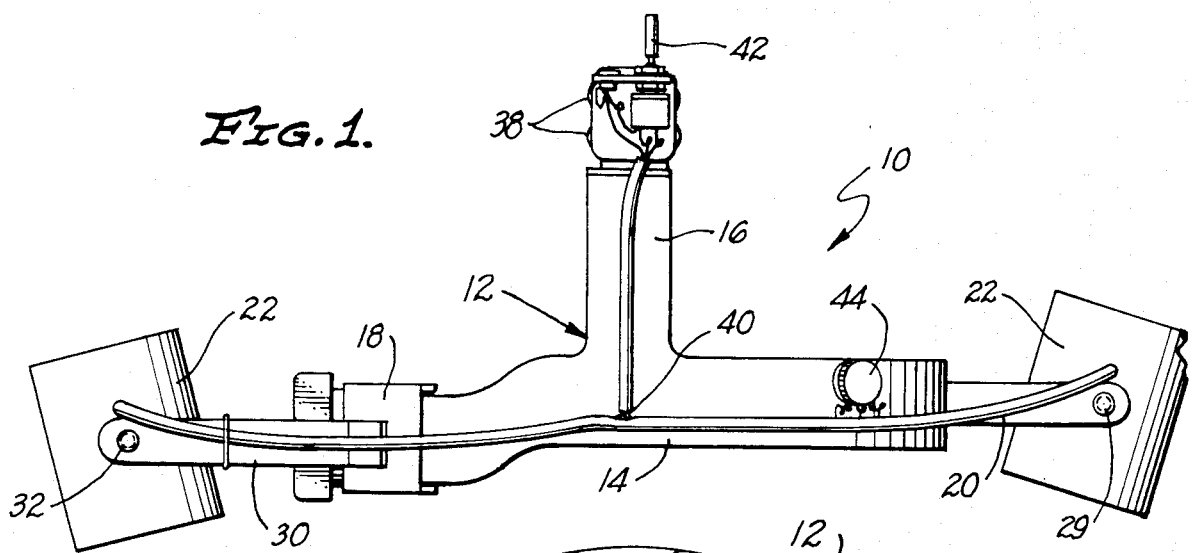
FIG. 1 is a side elevational view, partly fragmentary, of a surgeon's headpiece in accordance with this invention.

Considering now the drawing in greater detail, there is shown generally at 10 a surgeon's headpiece of preferred form in accordance with this invention. Serving as a frame on which other parts of the headpiece are mounted, is the plastic skeleton 12 of a welder's helmet, including a headband portion 14 (hereinafter referred to as headband 14) and an arched bridge portion 16 (hereinafter called bridge 16) integral with the headband portion. The headband 14 has the usual mechanism 18 for adjusting the headband to an individual surgeon's head size.

Secured by a U-shaped yoke 20 to the front of the headpiece is a fan assembly comprising a cylindrical housing 22 for a small electric motor 24 having a shaft 26 on which is mounted a plastic fan blade 28. The cylindrical housing 22 is pivotally mounted between the arms of the yoke 20 at pivot points 29 so as to be adjustable through a range of angles relative to the yoke. This permits the wearer to easily adjust the angle of airstream delivery by the fan assembly to achieve optimum cooling effect therefrom. The pivotal connections between the fan assembly and yoke 20 are of any conventional type to permit tilting movement of the former while retaining it against slippage in any given position.

Mounted at the rear of headband 14 at pivot points 32, between two arms 30 extending rearwardly therefrom, are a second cylindrical housing, electric motor, shaft and fan blade similar to, and bearing the same respective reference numerals as, housing 22, motor 24, motor shaft 26 and fan blade 28 at the front of the headpiece. The front yoke 20 and rear arms 30 are fixedly attached to headband 14 and adjusting mechanism 18, respectively, by fastening means 34 at the front and 36 at the rear of the headpiece. The rear fan assembly, like the front one, is angularly adjustable by the wearer for optimum cooling effect.

Figure 2:
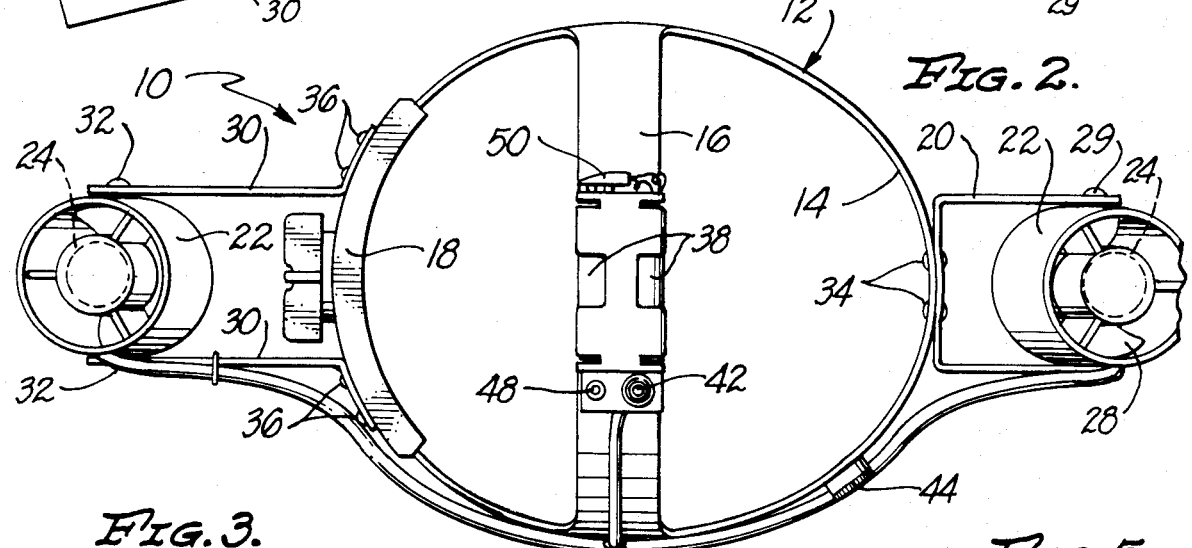
FIG. 2 is a top plan view, again partly framentary, thereof.
Figure 6:
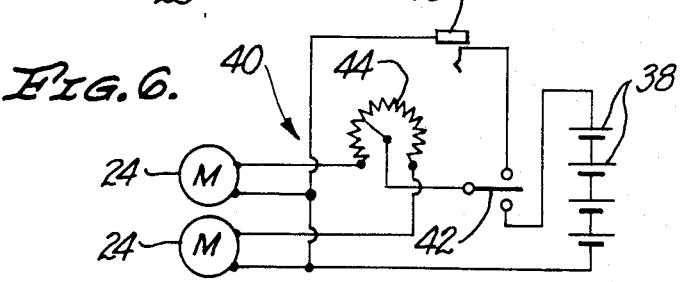
FIG. 6 is a circuit diagram of the wiring and electrical components of an electrical system forming part of the surgeon's headpiece.

Mounted on top of bridge 16 of headpiece 10 is a battery pack 38 containing four 1.5-volt batteries arranged in series. These batteries are connected to motor 24, mounted at the front, and its counterpart mounted at the rear, of the headpiece by means of suitable wiring 40 which is held in place by flexible plastic tubing. One or both of the front and rear fan motors can be energized to turn one or both of the fan blades for cooling effect by means of a switch 42 mounted on the battery pack 38. The speed of either fan blade can be controlled by means of a rheostat 44 mounted on the headband 14 at the position illustrated in FIGS. 1 and 2. As will shortly be seen, a prototype of battery pack 38 has proven itself capable of providing adequate power to headpiece fans in accordance with this invention for extended periods of time during long and arduous operations. Headpiece 10, however, has been provided with even greater power capacity by the incorporation of alternative means for powering its cooling fans, to render the fans functional as long as they are needed throughout an operation of any duration, by the incorporation within its circuitry of an AC-DC jack for a line from an AC to DC converter. Such a converter is shown at 48 in FIG. 6, and the jack at 50, in FIG. 2. The switch 42 is a two-way switch capable of an on position in either the converter circuit or the battery pack circuit. FIG. 6 is a circuit diagram of the components and wiring of the power system of of headpiece 10 and, as will be evident therefrom, when switch 42 is in the on position for either the converter- or battery-powered circuit, variation of rheostat 44 between its two extreme positions causes the speed of each fan for each of the two motors 24 to vary between zero and its maximum rpm. As the speed of one of the fan blades increases to its maximum rpm, through adjustment of the rheostat, that of the other fan blade decreases to zero. Thus by merely changing the rheostat setting, the speed of either the front or rear fan blade can be controlled to deliver a given air flow, or that of both fan blades can be adjusted for a desired cooling effect. While the illustrated circuit arrangement is the preferred one for our purpose, as presently contemplated, other circuitry can be substituted therefor within the scope of our invention if desired.

A surgeon's headpiece similar to that illustrated in the accompanying drawing has been tested by a surgeon in an operating room and found to have excellent cooling effect and to be so light in weight, in spite of the presence of the four batteries, that the surgeon was hardly aware of its presence after a short time. The fans on the headpiece were, according to the surgeon, easily adjustable to positions of optimum air distribution. This surgeon wore the headpiece while working in an operating room for six straight hours. He also wore it for three separate operations totalling twelve hours in all, and found that the batteries had not only maintained suitable fan speed for the entire twelve hours, but were still good after that. Although the weight of the batteries in the headpiece proved to be no burden to the surgeon during the many hours he was operating on patients, the batteries could have been removed and the headpiece powered by DC current from an AC to DC converter if he had felt it necessary to lighten the weight of the headpiece.

Figure 3:
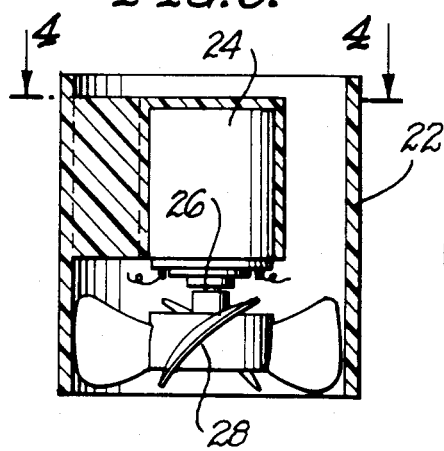
FIG. 3 is an enlarged view, mostly in longitudinal section, of a fan assembly forming part of the surgeon's headpiece.
Figure 4:
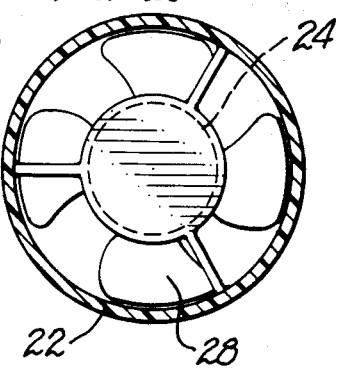
FIG. 4 is a cross-sectional view of the fan assembly taken along line 4—4 of FIG. 3.
Figure 5:
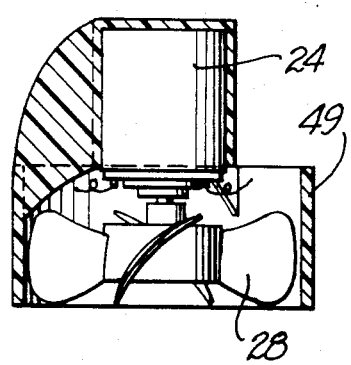
FIG. 5 is a view similar to FIG. 3, but showing an alternative fan assembly for the surgeon's headpiece.

As previously indicated, the secret of success of our illustrated fan assemblies resides in the fan housing arrangement of the assembly units and the manner in which their fan motors are mounted for use. Thus, in each case the housing for the fan is a cylindrical member open at both ends and having an inner diameter in close tolerance with the fan blade, as best illustrated in FIGS. 3, 4 and 5 of the drawing. Perhaps the single most important feature of he cooling units is the way in which the fan motors are attached to the cylindrical housing members. Thus, in each case, the motor is concentrically positioned with respect to the housing member and held there by means of three vanes 46 extending radially outwardly from the motor axis. These vanes are flat and relatively thin, and as a result of their geometric positioning relative to the housing members they present very little resistance to the air mass entering the housings. We have tested a great many arrangements for support of the fan motors, but have found only the vane concept described and illustrated herein capable of achieving the high volume of air flow exhibited by our novel fan units. While three vanes per unit are believed optimum for our purpose, the invention is not limited to that number of vanes. The fewer the number of vanes, however, the less blockage there will be of the entrance to the cylindrical housing member. It is not critically necessary that the vanes extend radially outwardly from the motor. Where they are not radial, however, their planes should be parallel to the housing axis so as to present minimal transverse blockage of the air passage through the housing member.

While heapiece 10 includes cooling units with cylindrical housings entirely surrounding the electric motors and fan blades of the fan assemblies, it is not essential, we have found, for the housing to actually encircle the motor it can, in fact, be even completely offset in the axial direction from the motor. FIG. 5 shows such an offset housing at 49. In that event the vanes connecting it to the motor bear the same cross-sectional relationship thereto as in the case of the units with motors disposed completely within the cylindrical housings. Thus, the two critical features of our fan assembly, that is, the close tolerance between the fan blade diameter and the inner wall of its cylingrical housing and the orientation of the motor support vanes relative to the housing axis, remain the same in either event. No prior art of which we are aware shows any kind of fan assembly with these two features. We do not completely understand the reasons why they contribute to such outstanding cooling success of our novel surgeon's headpiece, but we have tested scores of different cooling unit designs and observed that when our vane orientation and close fan blade tolerance with its housing are as taught herein, the fan assembly exhibits high performance capability, far and away superior to the performance of any prior art cooling unit of which we are aware. Proof of this resides in the fact that our prototype fan assemblies have achieved superior performance results during many hours of use under harsh operating conditions in a hospital.

While the present invention has been herein illustrated and described as a surgeon's headpiece, its use is not so limited, and the cooling units of this invention can be combined with any sort of a heapiece to provide colling for the face or back of the neck of its wearer or, as in the case of the illustrated headpiece, to both the front and back of the wearer's head. Its versatile adjustability as to the direction and volume of airflow and the focused nature and high volume of the airflow resulting from our unique cooling unit design guarantee effective cooling under oppressively hot working, or other, conditions. Because of the lack of channeling or focusing of the air output of any of the prior art headpiece cooling units of which we are aware, and the presence of obstructive grids, or the like, either side of the fan blade in those units, the units have very little cooling capability and are little more than novelty items. By contrast, our novel cooling units have proven themselves greatly effective in a difficult hopsital environment, without the aid of any auxiliary cooling device such as an air conditioning element of the type disclosed by Waters in his previously mentioned patents.

Our unique headpiece with its built-in cooling means has been herein illustrated and described in terms of reference to a preferred embodiment, but we wish to emphasize that the invention is not limited to that particular embodiment and is broad enough in scope to include various modifications thereof, some of which have been referred to above and others of which will occur to those skilled in the art in the light of the present teachings. All such modifications are, of course, within the scope of our invention insofar as encompassed by the language of the following claims.

We claim:

1. A headpiece with integrated cooling means comprising:
    a first electrically-powered fan assembly, including:
        a first fan blade;
        a first electric motor having a drive shaft drivingly connected to said first fan blade;
        first cylindrical housing means; and
        first support means interconnecting the first electric motor and first cylindrical housing means to position said first fan blade in the first cylindrical housing means in coaxial relationship therewith;
    said first fan blade being diametrically sized to fit within said first cylindrical housing means in close tolerance with its inner wall surface;
    said first support means comprising at least two flat vanes integral with and interconnecting said first electric motor and said first cylindrical housing means in planar positions presenting no surfaces greater than their transverse cross-sectional areas to block or divert the path of airflow through said first cylindrical housing means, thereby insuring minimal obstruction to said airflow; and
    said first fan assembly being positioned to blow air generally downwardly in front of the face of its wearer;
    a second electrically-powered fan assembly, including:
        a second fan blade;
        a second electric motor having a shaft drivingly connected to said second fan blade;
        second cylindrical housing means; and
        second support means interconnecting the second electric motor and second cylindrical housing means to position said second fan blade in the second cylindrical housing means in coaxial relationship therewith;
    said second fan blade being diametrically sized to fit within said second cylindrical housing means in close tolerance with its inner wall surface;
    said second support means comprising at least two flat vanes integral with an interconnecting said second electric motor and said second cylindrical housing means in planar positions presenting no surfaces greater than their transverse cross-sectional areas to block or divert the path of airflow through said second cylindrical housing means, thereby insuring minimal obstruction to that airflow; and
    said second fan assembly being positioned to blow air generally downwardly in back of the head of its wearer; and
    a welder's helmet frame, bracket means affixed to the front and back of the helmet frame and means pivotally securing the first and second fan assemblies to the bracket means whereby each of the assemblies can be manually pivoted to any desired position and remains in that position until pivoted to another position.

2. A headpiece in accordance with claim 1 including a battery pack for powering the fan motors, said battery pack being mounted on top of the welder's helmet frame.

3. A headpiece in accordance with claim 2 including an AC-DC jack for receiving current from an AC to DC converter to power said fan motors.

4. A headpiece in accordance with claim 3 including wiring and switch means to interconnect the fan motors alternatively with the battery pack or the AC to DC converter for the powering of said motors.

5. A headpiece in accordance with claim 4 including a rheostat forming with said wiring, said switch, said motors, said converter and said battery pack a circuit arrangement whereby each of said fan motors can be powered by either the AC to DC converter or the battery pack and adjusted by means of said rheostat between rpm limits of zero and maximum rpm while the other motor is concurrently adjusted by the rheostat in the opposite direction so that when one motor is running at its maximum rpm the other is not running.

6. A headpiece in accordance with claim 5 in which said at least two flat vanes are three flat vanes.

7. A headpiece in accordance with claim 6 in which said electric motor and said fan blade are axially aligned and said vanes are radially disposed with respect to the axis of said motor.

8. A headpiece in accordance with claim 7 in which said electric motor is of round cross section and is concentrically surrounded by said cylindrical housing.

9. A headpiece in accordance with claim 7 in which said electric motor extends at least partially away from the area encircled by said cylindrical housing.

* * * * *

UNITED STATES PATENT AND TRADEMARK OFFICE
CERTIFICATE OF CORRECTION

PATENT NO. : 4,672,968

DATED : June 16, 1987

INVENTOR(S) : JERRIL C. LENOX; JESSE SOLIS

It is certified that error appears in the above-identified patent and that said Letters Patent is hereby corrected as shown below:

Column 1, line 31, change "that" to --than--; and line 61, change "ventilaion" to --ventilation--. Column 2, line 47, "outwadly" should be --outwardly--; and line 67, "framentary" should be --fragmentary--. Column 4, line 9, cancel "of" after "system"; and line 54, change "he" to --the--. Column 5, line 42, "colling" should be --cooling--; and line 56, change "hopsital" to --hospital--. Column 6, line 34, insert --drive-- before "shaft".

Column 5, line 41, "heapiece" should read -- headpiece --.

Signed and Sealed this

Second Day of August, 1988

Attest:

DONALD J. QUIGG

Attesting Officer

Commissioner of Patents and Trademarks